United States Patent [19]

DeLuca et al.

[11] 4,307,025

[45] Dec. 22, 1981

[54] 1α, 25-DIHYDROXY-2β-FLUOROVITAMIN $D_3$

[75] Inventors: Hector F. DeLuca; Heinrich K. Schnoes, both of Madison, Wis.; Nobuo Ikekawa, Musashinoshi, Japan; Yoko Tanaka, Madison, Wis.; Masuo Morisaki; Jun-ichi Oshida, both of Tokyo, Japan

[73] Assignee: Wisconsin Alumni Research Foundation, Madison, Wis.

[21] Appl. No.: 235,262

[22] Filed: Feb. 17, 1981

[51] Int. Cl.[3] .............................................. C07J 9/00
[52] U.S. Cl. .................................................. 260/397.2
[58] Field of Search ..................................... 260/397.2

[56] References Cited

U.S. PATENT DOCUMENTS 4,263,214  4/1981  DeLuca et al. .................. 260/397.2

Primary Examiner—Elbert L. Roberts
Attorney, Agent, or Firm—Howard W. Bremer

[57] ABSTRACT

The invention provides new derivatives of vitamin $D_3$, specifically, 1α,25-dihydroxy-2β-fluorocholecalciferol.

The compound is characterized by vitamin D-like activity as measured by its ability to stimulate intestinal calcium transport, mobilization of calcium from bone, increase serum inorganic phosphorous and in their antirachitic activity. The compound, could, therefore, find ready application as a substitute for vitamin D in its various known applications and in the treatment of various metabolic bone diseases.

3 Claims, No Drawings

1α, 25-DIHYDROXY-2β-FLUOROVITAMIN D₃

DESCRIPTION

The invention described herein was made in the course of work under a grant or award from the Department of Health and Human Services and U.S. Japan Cooperative Grant INT-76-05793 and IPA No. 0001 awarded by the National Science Foundation.

TECHNICAL FIELD

This invention relates to a novel vitamin D compound.

More specifically, this invention relates to a fluorinated derivative of 1α,25-dihydroxyvitamin $D_3$.

Vitamin D is known to regulate calcium and phosphorus metabolism in animals and humans. It is now also generally accepted that the physiological action of vitamin D is dependent on the metabolism of the vitamin to hydroxylated forms. Thus vitamin $D_3$ is hydroxylated in vivo to 25-hydroxyvitamin $D_3$ which in turn is converted to 1α,25-dihydroxyvitamin $D_3$, and it is the latter compound specifically which is thought to regulate calcium and phosphorus homeostasis by promoting calcium and phosphorus transport in intestine and the mobilization of bone mineral.

Because of their high biological activity, these hydroxylated forms of vitamin D are important pharmaceutical products which have found use in the treatment of various bone disorders. In addition, many unnatural analogs of these hydroxylated vitamin D metabolites have been prepared in recent years, including some highly potent fluorinated vitamin D derivatives.

BACKGROUND ART

Vitamin D metabolites, analogs, and their preparation and application are discussed in many references in the patent and other literature, as for example, in U.S. Pat. No. 3,565,924 directed to 25-hydroxycholecalciferol; U.S. Pat. No. 3,697,559, directed to 1,25-hydroxycholecalciferol; U.S. Pat. No. 3,741,996 directed to 1α-hydroxycholecalciferol, and U.S. Pat. No. 3,907,843 directed to 1α-hydroxyergocalciferol. Fluorinated vitamin D derivatives and methods for preparing such compounds are the subject of U.S. Pat. No. 4,196,133 directed to 24,24-difluoro-25-hydroxyvitamin $D_3$; U.S. Pat. No. 4,201,881 directed to 24,24-difluoro-1α,25-dihydroxyvitamin $D_3$; and U.S. Pat. Nos. 4,188,345, 4,229,357, 4,229,358, 4,226,787 and 4,224,230.

DISCLOSURE OF INVENTION

Novel vitamin $D_3$ derivatives have now been found which exhibit very high biological activity. Such products, which can be readily prepared by the enzymatic hydroxylation of 2β-fluoro-1α-hydroxyvitamin $D_3$, and have been characterized as 1α,25-dihydroxy-2β-fluorovitamin $D_3$ and the 1-, 3-, and 25-acylates thereof. These compounds are conveniently represented by the following formula

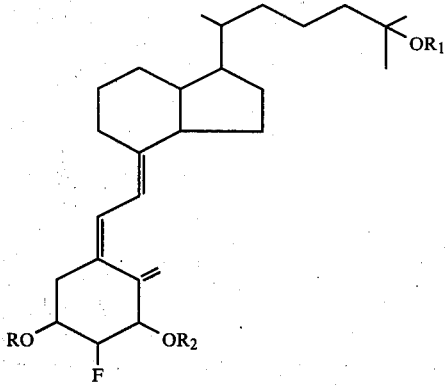

where each of R, $R_1$ and $R_2$ is selected from hydrogen and an acyl group having from 1 to about 6 carbon atoms. By virtue of their high biological potency the compounds of this invention would find application in the treatment of bone disorders.

BEST MODE FOR CARRYING OUT THE INVENTION 1,25-Dihydroxy-2β-fluorovitamin $D_3$ is readily prepared from 1α-hydroxy-2β-fluorovitamin $D_3$ by in vitro enzymatic hydroxylation of the latter compound at carbon 25.

Hydroxylation of 1α-hydroxy-2β-fluorovitamin $D_3$ is accomplished by incubating this compound with a homogenate prepared from liver tissue of vitamin D-deficient rats. The starting material 1α-hydroxy-2β-fluorovitamin $D_3$ is available by the synthesis of Oshida et al. (Tetrahedron Letters, 21, 1755–1756 (1980)) and is converted to the 25-hydroxy analog according to the following procedure.

Male weanling rats are fed vitamin D-deficient diet (Suda et al, J. Nutr. 100, 1049–1052, 1970) for one month. They are then killed, their livers are removed, and a 20% (w/v) homogenate is prepared in ice-cold 0.1 M phosphate buffer (pH 7.4) containing 0.25 M sucrose. Incubation is carried out in a 125 ml Erlenmeyer flask containing an aliquot of liver homogenate representing 1 g of liver tissue, suspended in 10 ml of incubation medium composed of the following materials at the concentrations indicated: 0.125 M sucrose, 50 mM phosphate buffer (pH 7.4), 22.4 mM glucose-6-phosphate, 20 mM ATP, 160 mM nicotinamide, 25 mM succinate, 0.4 mM NADP, 5 mM $MgCl_2$, 0.1 M KCl, 10 μg N,N'-diphenyl-p-phenylenediamine and 0.5 units glucose-6-phosphate-dehydrogenase. The reaction is initiated by addition of 10 μg 1α-hydroxy-2β-fluorovitamin $D_3$ dissolved in 25 μl 95% ethanol. The mixture is incubated at 37° C. with shaking at 100 oscillation/min for 2 hr. The reaction is stopped by addition of 20 ml methanol and 10 ml chloroform. After further addition of 10 ml chloroform and 6 ml $H_2O$ the organic phase is separated, evaporated, and the residue containing the desired 1,25-dihydroxy-2β-fluorovitamin $D_3$ is then subjected to chromatographic purification.

The residue is redissolved in 1 ml of $CHCl_3$:hexane (65:35) and applied to a Sephadex LH-20 column (0.7×14 cm) packed and equilibrated with the same solvent. The column is eluted with 36 ml of the same solvent. The first 11 ml is discarded while the next 25 ml is collected and evaporated. The residue is then dissolved in 10% 2-propanol in hexane and subjected to high performance liquid chromatography (Model ALC/GPC 204 high performance liquid chromatography, Waters Associates, Medford, MA) using a Zorbax-SIL column (4.6 mm×25 cm) (Dupont, Inc., Wilmington, DE) operating under pressure of 1,000 psi which produces a flow rate of 2 ml/min. The product collected is further purified by high performance chromatography using a reversed-phase column (Richrosorb RP-18; 4.6 mm×25 mm; E. Merck, Darmstadt, West Germany) operating at a pressure of 1,300 psi. The product eluted with a solvent mixture of $H_2O$:methanol (22:78) is collected, evaporated and once more chromatographed on the Zorbax-SIL column described above using conditions stated. After recycling twice, the pure substance is obtained for physical identification.

CHARACTERIZATION OF PRODUCT

The compound has a typical vitamin D absorption maximum at 265 nm and a minimum at 228 nm as determined in 95% ethanol with a Beckman model 24 recording spectrophotometer. These data show the presence of the 5,6-cis-triene chromophore.

The mass spectrum of the product contains a molecular ion at m/e 434 as required for a 1,25-dihydroxy-2$\beta$-fluorovitamin $D_3$, Fragments ions at m/e 416 and 398 represent elimination of one and two molecules of $H_2O$. Loss of the entire steroid side chain (cleavage of C17/C20)bond) results in the fragment of m/e 305 which by elimination of one and two molecules of $H_2O$, gives rise to the peaks at m/e 287 and 269. The spectrum also shows the very diagnostic fragment at m/e 170 (ring A+C$_6$+C$_7$) which by elimination of $H_2O$ gives the peak at m/e 152, whereas the alternative embodiment of HF gives the peak at m/e 150. In addition the spectrum shows a prominent fragment peak at m/e 59 which results from cleavage of the C24/C25 bond and corresponds to the ion $((CH_3)_2C=^+OH)$; the presence of this ion is characteristic for 25-hydroxylated vitamin D compounds and thus confirms the presence of a 25-hydroxy group in the product obtained. These data establish that the product obtained from enzymatic hydroxylation of 1$\alpha$-hydroxy-2$\beta$-fluorovitamin $D_3$ is 1$\alpha$,25-dihydroxy-2$\beta$-fluorovitamin $D_3$.

The aforesaid vitamin D derivative, 1$\alpha$,25-dihydroxy-2$\beta$-fluorovitamin $D_3$, can be readily obtained in crystalline form by recrystallization from a suitable solvent or solvent system e.g. ethanol. Acylated derivatives of 1$\alpha$,25-dehydroxy-2$\beta$-fluorovitamin $D_3$ are readily prepared by acylation of the compound with acyl anhydrides or acyl halides as is well known in the art. Thus reaction of 1$\alpha$,25-dihydroxy-2$\beta$-fluorovitamin $D_3$ with acetic anhydride in pyridine at room temperature yields the 1,3-diacetate derivative, whereas reaction at elevated temperatures (60°–100° C.) yields the corresponding 1,3,25-triacetylated compound. Further it is possible to hydrolyze selectively certain acyl groups of the triacetylated derivative to obtain other partially acylated products. For example, base hydrolysis (KOH/MeOH, 30°–50°, 1–2 hr.) of 1$\alpha$,25-dihydroxy-2$\beta$-fluorovitamin $D_3$ 1,3,25-triacetate yields the 1$\alpha$,25-dihydroxy-2$\beta$-fluorovitamin $D_3$-25-monoacetate which can be acylated to introduce different acyl groups at C-1 and C-3. It is thus obvious that by a combination of acylation and/or hydrolysis reactions a variety of partially or fully acylated derivatives, where the acyl groups are the same or different, can be prepared.

BIOLOGICAL ACTIVITY

The biological activity of the new analog can be demonstrated by an in vivo assay in the rat. Male weanling rats are fed a low calcium vitamin D-deficient diet (J. Nutr. 100, 1045–1052, 1970) for 3 weeks. They are then divided into three groups of 5–6 rats each. The rats of control group are given 0.05 ml of 95% ethanol by intrajugular injection. The rats of the second group are administered in same manner a dose of 650 pmole of 1$\alpha$,25-dihydroxy-2$\beta$-fluorovitamin $D_3$ (1$\alpha$,25-$(OH)_2$-2$\beta$-F-$D_3$) dissolved in 0.05 ml of 95% ethanol, while the rats of the third group are injected with a dose of 650 pmole of 1$\alpha$,25-dihydroxyvitamin $D_3$ (1$\alpha$,25-$(OH)_2D_3$) for comparative purposes. Twenty-four hours after dosing, the effect of the test compounds on intestinal calcium transport and on bone calcium mobilization (measured by the rise of serum calcium concentration) are determined by assay procedures of Martin & DeLuca (Am. J. Physiol. 216, 1351–1359 (1969)) and of Tanaka et al. (Biochemistry 14, 3293–3296 (1975)) respectively, with the following results:

| Biological activity of 1$\alpha$,25-$(OH)_2$-2$\beta$-F-$D_3$ | | |
| --- | --- | --- |
| Compound given | Intestinal calcium transport (ca serosal/Ca mucosal) | Bone calcium mobilization Serum calcium (mg/100 ml) |
| EtOH(Control) | 3.4 ± 1.0*,a | 4.3 ± 0.1d |
| 1$\alpha$,25-$(OH)_2$-2$\beta$-F-$D_3$ | 6.0 ± 0.6b | 5.1 ± 0.4e |
| 1$\alpha$,25-$(OH)_2D_3$ | 5.3 ± 0.9c | 5.1 ± 0.3e |

*Standard deviation of the mean
Significance of difference: b from a, $p<0.001$; c from a, $p<0.01$; e from d, $p<0.001$.

The foregoing data indicate that 1,25-dihydroxy-2$\beta$-fluorovitamin $D_3$ is active both in intestine and in bone and, further, that this new compound is at least as potent as 1$\alpha$,25-dihydroxyvitamin $D_3$, which is considered to be the most active metabolite of vitamin $D_3$ known.

1,25-dihydroxy-2$\beta$-fluorovitamin $D_3$ may be readily administered as sterile parenteral solutions, by injection or intravenously, or by alimentary canal in the form of oral dosages or by suppository. Doses of from about 0.1 $\mu$g to about 2.5 $\mu$g per day would appear to be effective in obtaining the physiological calcium balance responses characteristic of vitamin D-like activity with maintenance dosage of from about 0.1 $\mu$g to about 0.5 $\mu$g being suitable.

Dosage forms of the compound can be prepared by combining it with a non-toxic pharmaceuitcally acceptable carrier as is well known in the art. Such carriers may be either solid or liquid such as, for example, corn starch, lactose, sucrose, peanut oil, olive oil, sesame oil and water. If a solid carrier is used the dosage forms of the compounds of the invention may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

It should be understood that although dosage ranges are given the particular dose to be administered to a host will depend upon the specific disease state being treated, the end results being sought in a particular case, as well as other factors known to those skilled in the art in the therapeutic use of such medicinal agents.
We claim:
1. Compounds having the formula:
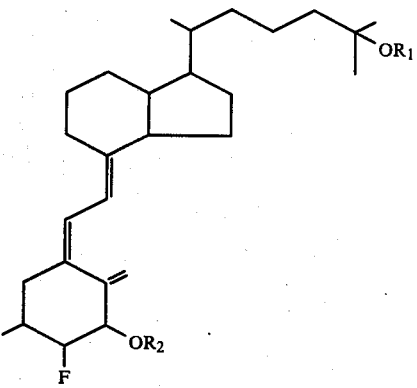
where each of R, $R_1$ and $R_2$ is selected from the group consisting of hydrogen and an acyl group having from 1 to about 6 carbon atoms.
2. 1α,25-dihydroxy-2β-fluorovitamin $D_3$.
3. The compound of claim 2 in crystalline form.
* * * * *